(12) United States Patent
Salinas Martín (10) Patent No.: US 10,463,670 B2
(45) Date of Patent: Nov. 5, 2019

(54) USE OF NON-PEPTIDE NK1 ANTAGONISTS IN A PREDETERMINED DOSE FOR THE TREATMENT OF CANCER

(71) Applicant: SERVICIO ANDALUZ DE SALUD, Seville (ES)

(72) Inventor: Manuel Vicente Salinas Martín, Seville (ES)

(73) Assignee: SERVICIO ANDALUZ DE SALUD, Seville (ES)

( * ) Notice: Subject to any disclaimer, the term of this patent is extended or adjusted under 35 U.S.C. 154(b) by 0 days.

(21) Appl. No.: 15/634,348

(22) Filed: Jun. 27, 2017

(65) Prior Publication Data

US 2018/0071301 A1    Mar. 15, 2018

Related U.S. Application Data

(63) Continuation of application No. 15/107,623, filed as application No. PCT/ES2014/000222 on Dec. 26, 2014, now abandoned.

(30) Foreign Application Priority Data

Dec. 27, 2013  (ES) .................................. 201331923

(51) Int. Cl.
*A61K 31/5377* (2006.01)
*A61K 45/06* (2006.01)
*A61K 33/24* (2019.01)

(52) U.S. Cl.
CPC .......... *A61K 31/5377* (2013.01); *A61K 33/24* (2013.01); *A61K 45/06* (2013.01)

(58) Field of Classification Search
CPC .... A61K 31/5377; A61K 33/24; A61K 31/58; A61K 45/06
See application file for complete search history.

(56) References Cited

U.S. PATENT DOCUMENTS

| | | | |
|---|---|---|---|
| 6,194,436 B1 | 2/2001 | Howard | |
| 6,576,638 B1 | 3/2003 | Pompei et al. | |
| 7,487,236 B2 | 2/2009 | Zabihi et al. | |
| 2009/0012086 A1* | 1/2009 | Munoz Saez | A61K 31/445 514/236.2 |
| 2009/0012087 A1 | 1/2009 | Branalt et al. | |
| 2014/0079665 A1 | 3/2014 | Goetsch et al. | |
| 2015/0297613 A1* | 10/2015 | Salinas Martin | A61K 31/5377 424/85.2 |
| 2016/0324881 A1 | 11/2016 | Bergmann | |
| 2018/0071317 A1 | 3/2018 | Salinas Martin et al. | |

FOREIGN PATENT DOCUMENTS

| | | |
|---|---|---|
| EP | 0773026 A2 | 5/1997 |
| ES | 2246687 A1 | 2/2006 |
| WO | 0101922 A2 | 1/2001 |
| WO | 2007039883 A2 | 4/2007 |
| WO | 2009124756 A1 | 10/2009 |
| WO | 2013087964 A1 | 6/2013 |
| WO | 2015101596 A2 | 7/2015 |

OTHER PUBLICATIONS

International Search Report, dated Mar. 30, 2015.
Munoz, Berger M, et al.; "Antitumor activity of neurokinin-1 receptor antagonists in MG-63 human osteosarcoma kenografts," International Journal of Oncology, 2014, pp. 137-146, vol. 44.
Langford, Patrick, et al.; "Fosaprepitant and aprepitant: an update of the evidence for their place in the prevention of chemotherapy-induced nausea and vomiting," Core Evidence, 2010, pp. 77-90, vol. 5.
European Search Report dated Mar. 27, 2019 for European Patent Application No. 14873139.1.
Adams, Gregory P., et al.; "Monoclonal antibody therapy of cancer," Nature Biotechnology, 2005, pp. 1147-1157, vol. 23.
Barker, R., "Tachykinins, neurotrophism and neurodegenerative diseases: a critical review on the possible role of tachykinins in the aetiology of CNS diseases," Reviews in the Neurosciences, 1996, pp. 187-214, vol. 7; Abstract Only.
Berzofsky, Jay A., et al.; "Progress on new vaccine strategies for the immunotherapy and prevention of cancer," The Journal of Clinical Investigation, 2004, pp. 1515-1525, vol. 113.
Bigioni, Mario, et al.; "Role of NK-1 and NK-2 tachykinin receptor antagonism on the growth of human breast carcinoma cell line MDA-MB-231," Anti-Cancer Drugs, 2005, pp. 1083-1089, vol. 16.
Bunn, Paul A., et al.; "Effects of Neuropeptide Analogues on Calcium Flux and Proliferation in Lung Cancer Cell Lines," Cancer Research, 1994, pp. 3602-3610, vol. 54.
Carmeliet, Peter, et al.; "Angiogenesis in cancer and other diseases," Nature, 2000, pp. 249-257, vol. 407.
Cox, Giles, et al.; "Matrix Metalloproteinase 9 and the Epidermal Growth Factor Signal Pathway in Operable Non-Small Cell Lung Cancer," Clinical Cancer Research, 2000, pp. 2349-2355, vol. 6.
Coussens, Lisa M., et al.; "Inflammation and cancer," Nature, 2002, pp. 860-867, vol. 420.
De Bari, Cosimo, et al.; "Multipotent Mesenchymal Stem Cells From Adult Human Synovial Membrane," Arthritis & Rheumatism, 2001, pp. 1928-1942, vol. 44.
De Visser, Karin E., et al.; "Paradoxical roles of the immune system during cancer development," Nature Reviews. Cancer, 2006, pp. 24-37, vol. 6.
Doi, Takayuki, et al.; "Effects of TAF-637, a tachykinin receptor antagonist, on lower urinary tract function in the guinea pig," European Journal of Pharmacology, 1999, pp. 297-303, vol. 383.
Giardina, G.A., et al.; "Antagonists at the neurokinin receptors—Recent patent literature," Drugs, 2003, pp. 758-772, vol. 6; Abstract Only.

(Continued)

*Primary Examiner* — Sudhakar Katakam
(74) *Attorney, Agent, or Firm* — Tristan A. Fuierer; Olive Law Group, PLLC (57) ABSTRACT

Use of the non-peptide NK1 receptor antagonist, preferably Aprepitant, for the treatment of cancer in predetermined doses. The present invention also describes pharmaceutical compositions comprising said agents, alone or in combination with at least one other active principle, for the treatment of cancer.

8 Claims, 4 Drawing Sheets

(56) References Cited

OTHER PUBLICATIONS

Hagemann, Thorsten, et al.; "Investigating Macrophage and Malignant Cell Interactions In Vitro," Methods in Molecular Biology, 2009, pp. 325-332, vol. 512.
Hanahan, Douglas, et al.; "The Hallmarks of Cancer," Cell, 2000, pp. 57-70, vol. 100.
Ikushima, Hiroaki, et al.; "TGFβ signalling: a complex web in cancer progression," Nature Reviews, Cancer, 2010, pp. 415-424, vol. 10.
Kramer, Mark S., et al.; "Distinct Mechanism for Antidepressant Activity by Blockade of Central Substance P Receptors," Science, 1998, pp. 1640-1645, vol. 281.
Lin, Wan-Wan, et al.; "A cytokine-mediated link between innate immunity, inflammation, and cancer," The Journal of Clinical Investigation, 2007, pp. 1175-1183, vol. 117.
Maggi, Carlo Alberto, et al.; "Tachykinin receptors and tachykinin receptor antagonists," Journal of Autonomic Pharmacology, 1993, pp. 23-93, vol. 13.
McAllister, Sandra S., et al.; "Tumor-Host Interactions: A Far-Reaching Relationship," Journal of Clinical Oncology, 2010, pp. 4022-4028, vol. 28.
Munoz, Miguel, et al.; "The NK-1 receptor is expressed in human melanoma and is involved in the antitumor action of the NK-1 receptor antagonist aprepitant on melanoma cell lines," Laboratory Investigation, 2010, pp. 1259-1269, vol. 90.
Orosz, Antal, et al.; "New Short-Chain Analogs of a Substance-P Antagonist Inhibit Proliferation of Human Small-Cell Lung-Cancer Cells In Vitro and In Vivo," International Journal of Cancer, 1995, pp. 82-87, vol. 60.
Palma, Carla, et al.; "The role of tachykinins via NK1 receptors in progression of human gliomas," Life Sciences, 2000, pp. 985-1001, vol. 67.
Quartara, L., et al.; "The tachykinin NK1 receptor. Part II: distribution and pathophysiological roles," Neuropeptides, 1998, pp. 1-49, vol. 32.
Rosso, Marisa, et al.; "The NK-1 Receptor Is Expressed in Human Primary Gastric and Colon Adenocarcinomas and Is Involved in the Antitumor Action of L-733,060 and the Mitogenic Action of Substance P on Human Gastrointestinal Cancer Cell Lines," Tumor Biology, 2008, pp. 245-254, vol. 29.
Singh, Deeppreet, et al.; "Increased expression of preprotachykinin-I and neurokinin receptors in human breast cancer cells: Implications for bone marrow metastasis," Proceedings of the National Academy of Sciences, 2000, pp. 388-393, vol. 97.
Welt, Sydney, et al.; "Antibody Targeting in Metastatic Colon Cancer: A Phase I Study of Monoclonal Antibody F19 Against a Cell-Surface Protein of Reactive Tumor Stromal Fibroblasts," Journal of Clinical Oncology, 1994, pp. 1193-1203, vol. 12.
Fielding, J., et al., "A Randomized Double-Blind Placebo-Controlled Study of Marimastat in Patients with Inoperable Gastric Adenocarcinoma," Proceedings of ASCO, Gastrointestinal Cancer, 2000, vol. 19, *929.
Rosemurgy, J., et al., "A Randomized Study Comparing Marimastat to Gemcitabine as First Line Therapy in Patients with Non-Resectable Pancreatic Cancer," Proceedings of ASCO, Gastrointestinal Cancer, 1999, vol. 19, *1005.
Sparano, J.A., et al., Randomized phase III trial of marimastat versus placebo in patients with metastatic breast cancer who have responding or stable disease after first-line chemotherapy: an Eastern Cooperative Oncology Group trial (E2196), Proceedings of ASCO, Breast Cancer, 2002, vol. 21, *173.
Takahashi et al.; "Pharmacokinetics of aprepitant and dexamethasone after adimistration of chemotherapeutic agents and effects of plasma substance P concentration on chemotherapy-induced nausea and vomiting in Japanese cancer patients," Cancer Chemother. Pharmacol., 2011, pp. 653-659, vol. 68.
Munoz et al.; "A new frontier in the treatment of cancer: NK-1 receptor antagonists," Current Medicinal Chemistry, 2010, vol. 17, pp. 504-516.
Munoz et al.; "NK-1 receptor Antagonists: A New Paradigm in Pharmacological Therapy," Current Medicinal Chemistry, 2011, vol. 18, pp. 1820-1831.
Sylvie Brener et al.; "A Role for the Substance P/NK-1 Receptor Complex in Cell Proliferation in Oral Squamous Cell Carcinoma," Anticancer Research Journal of Cancer Research and Treatment, 2009, vol. 29, pp. 2323-2329.
Office Action dated Oct. 10, 2018 for U.S. Appl. No. 15/634,358.
Office Action dated Jun. 18, 2019 for U.S. Appl. No. 15/634,358.
Lexico; Definition of composition in English: composition; https://www.lexico.com/en/definition/composition; accessed Mar. 12, 2019 (year: 2019).

* cited by examiner

USE OF NON-PEPTIDE NK1 ANTAGONISTS IN A PREDETERMINED DOSE FOR THE TREATMENT OF CANCER

CROSS-REFERENCE TO RELATED APPLICATIONS

This application is filed under the provisions of 35 U.S.C. § 111(a) and is a continuation of U.S. patent application Ser. No. 15/107,623 filed on Jun. 23, 2016, and entitled "USE OF NON-PEPTIDE NK1 ANTAGONISTS IN A PREDETERMINED DOSE FOR THE TREATMENT OF CANCER" in the name of Manuel Vicente SALINAS MARTIN, which claims priority to International Patent Application No. PCT/ES2014/000222 filed on 26 Dec. 2014, which claims priority to Spanish Patent Application No. 201331923 filed on Dec. 27, 2013, all of which are hereby incorporated by reference herein in their entirety.

FIELD OF THE INVENTION

The present invention is within the field of molecular biology applied to medicine, pharmacology and oncology. Specifically, it is related to the use of anti-tumour agents, more specifically non-peptide NK1 receptor antagonists, in predetermined doses, for the manufacturing of medicaments of use in the treatment of cancer in mammals and, more preferably, in humans.

BACKGROUNDS OF THE INVENTION

NK1 receptors (neuropeptide receptors of Substance P and tachykinins), are widely distributed in the organism's cells. Their presence has been verified in the central and peripheral nervous system of mammals, in the digestive apparatus, in the circulatory system, in haematopoietic and inflammatory and/or immune response cell lines cells, as well as in soft tissues and especially in vascular endothelium. Numerous biological processes are currently known in which regulation NK1 receptors are involved.

Substance P (SP), is the preferred agonist of the NK1 receptor, it is a undecapeptide produced naturally in mammals, it belongs to tachykinin family and its sequence was described by Veber et al. (U.S. Pat. No. 4,680,283). The tachykinin family also includes other peptides such as Neurokinin A, Neurokinin B, Neuropeptide K, Neuropeptide Gamma and Hemokinin I, among others.

The scientific bibliography has widely referred to the involvement of SP and other tachykinins in the aetiopathogenesis of various diseases of the human nervous system such as Alzheimer's Disease, Multiple Sclerosis, Parkinson's Disease, anxiety and depression (Barker et al., 1996. *Neurosci. Res.* 7, 187-214; Kramer et al., 1998. *Science* 11; 281(5383), 1640-5). The involvement of tachykinins has also been verified in the etiopathogenesis of various diseases such as rheumatoid arthritis, asthma, allergic rhinitis, inflammatory intestinal diseases such as ulcerative colitis and Crohn's disease (Maggi et al., 1993. *Journal of Autonomic Pharmacology* 13, 23-93).

In this sense, non-peptide NK1 receptor antagonists have been developed as medicaments for the treatment of various central nervous system disorders such as depression, psychosis and anxiety (WO 95/16679, WO 95/18124, WO 95/23798 and WO 01/77100). It has been disclosed that the use of selective NK1 receptor antagonists is useful in the treatment of nauseas and vomiting induced by antineoplastic chemotherapies and in the treatment of certain forms of urinary incontinence (Quartara et al., 1998. *Neuropeptides* 32(1), 1-49; Doi et al., 1999. *Eur. J. Pharmacol.* 383(3), 297-303).

In a work published in 2003 (Giardina et al., 2003. *IDrugs* 6(8), 758-72.), a review was made of the more recent patents on NK1 receptor antagonists. The molecules of the most important global manufacturers are described with indication of their possible applications, among which we can highlight: anti-depressive, anti-inflammatory, anxiolytic, antiemetic, treatment of ulcerative colitis and others.

It has been demonstrated that NK1 and SP receptor antagonists may inhibit the proliferation of lung cancer cells (Orosz et al., 1995. *Int. J. Cancer* 60(1), 82-7, Bunn et al., 1994. *Cancer Res.* 54(13), 3602-10), brain tumours (Palma et al., 2000. *Life Sci.* 67(9), 985-1001), APUDOMAS (enterochromaffin cell tumours; patent EP 773026), prostate cancers (patent WO 2001001922), stomach and colon cancers (Rosso et al., 2008. *Tumour Biol.* 29(4), 245-54), melanoma (Munoz et al., 2010. *Lab. Invest.* 90(8), 1259-69).

Various studies with specific antagonists of neurokinin NK receptors such as CP-96341-1 (Pfizer), MEN 11467, SR 48968 (Sanofi) and MEN 11420 (Nepadutant) have demonstrated the efficacy thereof in blocking cell proliferation (Singh et al., 2000. *Proc. Natl. Acad. Sci.* 97(1), 388-93; and Bigioni et al., 2005. *Anticancer Drugs* 16(10), 1083-9.).

Patent ES 2246687 claims the use of non-peptide NK1 and SP receptor antagonists in the preparation of a pharmaceutical composition for the production of apoptosis in tumour cells of mammals.

In the genesis and development of cancer there is not just the intervention of molecular mechanisms typical of tumour cells, but the cells surrounding the tumour have great importance (specifically stroma cells and inflammatory cells), as well as the interactions that take place between the tumour cells and these cells surrounding the tumour (McAllister et al., 2010. *J. Clin. Oncol.* 28(26), 4022-8; Ikushima et al., 2010. *Nat. Rev. Cancer* 10(6), 415-24). In this sense, it has been published that some substances, e.g. nuclear factor NF-KB (nuclear factor kappa B), SPARC (secreted protein acidic, cysteine-rich), TGF-α and TGFβ (transforming growth factors α and β, respectively) or Metalloproteinase (MMPs), are present in the tumour microenvironment and are of great importance in the genesis and progression of tumours (Coussens et al., 2002. *Nature* 19-26; 420(6917), 860-7; Berzofsky et al., 2004. *J. Clin. Invest.* 113, 1515-1525; Carmeliet et al., 2000. *Nature* September 14; 407 (6801), 249-57; Hanahan et al., 2000. *Cell* January 7; 100(1), 57-70).

It is known that the cells surrounding the tumour (specifically the stroma cells and inflammatory cells) express a large amount of the NK1 receptor and that NK1 receptor antagonists modulate the production of these substances by the cells surrounding the cancerous tumours, preventing the survival and progression of these tumours (patent PCT/ES2012/070865).

Therefore, and in conclusion, nowadays the following facts are known in the state of the art:

1. That NK1 receptors are widely disseminated in the human organism.
2. That tachykinins and, in particular, SP act on the NK1 receptors.
3. That the use of non-peptide NK1 receptor antagonists is possible for the preparation of a medicament for the treatment of various central nervous system disorders such as depression, psychosis and anxiety which have been object of claim in various patent applications (WO 95/16679, WO 95/18124, WO 95/23798 and WO 01/77100).
4. That the use of non-peptide NK1 receptor antagonists has demonstrated effects on tumour cells, which results in their cell death by apoptosis (ES 2246687) in in vitro tumour cell cultures.
5. That, as it has been mentioned, patent ES 2 246 687 claims the use of non-peptide NK1 receptor antagonists to induce death and apoptosis in tumour cells (and it lists specifically a number thereof). Therefore, it does not include the effects that non-peptide NK1 receptor antagonists may perform at a level of substances and cells that compose the tumour microenvironment, which are of vital importance for the genesis, development and progression of tumours.
6. The presence of NK1 receptors has been demonstrated in blood cells involved in the inflammatory and/or immune response, in cells of the stromal matrix and in the vascularization cells that surround tumour cells. It is known that stromal cells, blood cells involved in the inflammatory and/or immune response and the vascularization cells, influence the evolution of malignant tumours.
7. It has been demonstrated that NK1 receptor antagonists may prevent the survival and progression of tumours by means of modulating the functioning of the microenvironment cells.

However, the known precedents, which include the use of non-peptide NK1 receptor antagonists to cause death (apoptosis) in tumour cells and the modification of the peritumoral environment by means of the induction of changes in the cells forming said environment and in the substances secreted by them, with the aim of preventing or hindering the genesis, development or progression of tumours, at present, there is controversy about the effect of the in vivo use of NK1 receptor antagonists for the treatment of cancerous tumour disease (Harford-Wrigth et al., *Drug Discovery,* 2013, 8, 13-23). In this sense, the data published in vivo are contradictory (Palma C, et al., *Br J Cancer* 2000; 82: 480-7; Bigioni M, et al. *Anticancer Drugs* 2005, 16, 1083-9), so that in some cases the use of NK1 receptor antagonists (such as Aprepitant) cause reduction in the tumour size in experimental animal models (in vivo) and in other cases does not produce them. In particular, in a recently published work, the use of Aprepitant at doses of 3 mg per kilogram of weight and day, does not cause a reduction in brain tumour sizes in animal experimentation models in mice (Lewis K M, et al., *Anti-Cancer Drugs* 2013, 24, 344-354).

Therefore, the efficacy of Aprepitant as treatment of cancerous tumours in animals (including human beings) is not a "universal" effect but dependent on dose and tumour type.

Thus, the object of the present invention and the technical advantage it provides, is the use of non-peptide NK1 receptor antagonists for the treatment of cancer, in a predetermined dose range, for the manufacturing of a medicament or pharmaceutical composition, by suitable administration route and at suitable doses, of use in the therapeutic treatment of cancer by direct administration to a mammal, including humans.

The fact that the invention influences cancer treatment through the use of suitable doses to reduce tumour sizes, prevent their development and, possibly, induce their disappearance, makes it possible to adjust the effective doses of anti-tumour agents both based on chemotherapy and radiotherapy, and the nature of the combinations to be performed therewith. This entails a more effective treatment, with a broader spectrum in treatable tumours, at possibly more adjusted doses, which involves less associated secondary effects and better quality of life for the patients during and after treatment.

BRIEF DESCRIPTION

The present invention reveals that much greater doses are required than are described in the administration of NK1 agonists, so that they exercise their anti-tumour effect.

Therefore, a first aspect of the present invention relates to the use of a non-peptide NK1 receptor antagonist at doses between 5 and 120 mg/kg of weight per day, hereinafter non-peptide NK1 receptor antagonist in a predetermined dose of the invention, in the preparation of a medicament for the treatment of cancer in a mammal. In a preferred embodiment of this aspect of the invention, the dose is between 8 and 100 mg/kg of weight per day. Even more preferably, the dose is between 10-80 mg/kg of weight per day. In another even much more preferred embodiment, the dose is between 30 and 50 mg/kg of weight per day, and even much more preferably between 35 and 45 mg/kg of weight per day. In a particular embodiment, it is of approximately 40 mg/kg of weight per day.

In another preferred embodiment, the non-peptide NK1 receptor antagonists are selected from the list consisting of: Aprepitant, Vestipitant, Casopitant, Vofopitant, Ezlopitant, Lanepitant, LY-686017, L-733,060, L-732,138, L-703,606, WIN 62,577, CP-122721, TAK-637, and R673, CP-100263, WIN 51708, CP-96345, L-760735, CP-122721, L-758298, L-741671, L-742694, CP-99994, T-2328, or any combinations thereof. In a more specific embodiment, are especially preferred the antagonists selected from: Aprepitant, Vestipitant, Casopitant, Vofopitant, Ezlopitant and Lanepitant, or any combinations thereof. Even much more preferably, the non-peptide NK1 receptor antagonist is Aprepitant.

In another preferred embodiment of this aspect of the invention, the cancer is selected from the list comprising: gastric cancer, colon cancer, pancreatic cancer, breast cancer, ovarian cancer, endometrial cancer, choriocarcinoma, uterine cervical cancer, lung cancer, thyroid cancer, bladder cancer, prostate cancer, glial tumours of the central nervous system, sarcomas, melanomas, embryonal carcinoma and haematological malignancies. In another more preferred embodiment, the cancer presents alteration of the peritumoral environment. In another more preferred embodiment, the cancer that presents alteration of the peritumoral environment shows an increased synthesis of the markers selected from the list consisting of: NF-kB, EGF, VEGF, TNF-α, TGF-α, TGF-β1, TGF-β2, TGF-β3, SPARC, MMP-3; MMP-7, MMP-9, MMP-11, MMP-13, MMP-14 and/or combinations thereof.

In another preferred embodiment, the mammal is human. Even more preferably, the cells of the tumour object of this invention overexpress the markers NF-kB, EGF, VEGF, TNF-α, TGF-α, TGF-β1, TGF-β2, TGF-β3, SPARC, MMP-3; MMP-7, MMP-9, MMP-11, MMP-13, MMP-14 and/or combinations thereof.

A second aspect of the invention relates to the use of a combined preparation comprising a non-peptide NK1 receptor antagonist in a predetermined dose of the invention, in combination with at least one active principle, hereinafter active principle B of the invention, which induces apoptosis in the tumour cells, in the preparation of a medicament for the treatment of cancer. In a preferred embodiment, the non-peptide NK1 receptor antagonist in a predetermined dose is selected from the list consisting of: Aprepitant, Vestipitant, Casopitant, Vofopitant, Ezlopitant, Lanepitant, LY-686017, L-733,060, L-732,138, L-703,606, WIN 62,577, CP-122721, TAK-637, and R673, CP-100263, WIN 51708, CP-96345, L-760735, CP-122721, L-758298, L-741671, L-742694, CP-99994, T-2328, or any combinations thereof. In a more specific embodiment, being especially preferred the antagonists selected from: Aprepitant, Vestipitant, Casopitant, Vofopitant, Ezlopitant and Lanepitant, or any combinations thereof. Even much more preferably, the non-peptide NK1 receptor antagonist is Aprepitant.

In another preferred embodiment of this aspect of the invention, the active principle which induces apoptosis in the tumour cells is selected from the list consisting of: Chlorambucil, Melphalan, Aldesleukin, 6-Mercaptopurine, 5-Fluorouracil, Ara-c, Bexarotene, Bleomycin, Capecitabine, Carboplatin, Cisplatin, Docetaxel, Doxorubicin, Epirubicin, Fludarabine, Irinotecan Methotrexate, Mitoxantrone, Oxaliplatin, Paclitaxel, Rituximab, Vinblastine, Etoposide, Teniposide, Vincristine, Vinorelbine, Imatinib, Erlotinib, Cetuximab, Trastuzumab, or any combinations thereof.

In another preferred embodiment of this aspect of the invention, the non-peptide NK1 receptor antagonist of the invention and the active principle B of the invention (active principle which induces apoptosis) is administered separately, jointly or sequentially, and can be combined with at least one other anti-cancer agent selected from a chemotherapy agent or a radiotherapy agent.

In another preferred embodiment of this aspect of the invention, the cancer is selected from the list consisting of: gastric cancer, colon cancer, pancreatic cancer, breast cancer, ovarian cancer, endometrial cancer, choriocarcinoma, uterine cervical cancer, lung cancer, thyroid cancer, bladder cancer, prostate cancer, glial tumours of the central nervous system, sarcomas, melanomas, embryonal carcinoma and haematological malignancies. In another more preferred embodiment, the cancer presents with alteration of the peritumoral environment. In another more preferred embodiment, the cancer that presents with alteration of the peritumoral environment shows an increased synthesis of the following markers selected from the list comprising: NF-kB, EGF, VEGF, TNF-$\alpha$, TGF-$\alpha$, TGF-$\beta$1, TGF-$\beta$2, TGF-$\beta$3, SPARC, MMP-3; MMP-7, MMP-9, MMP-11, MMP-13, MMP-14 and/or combinations thereof.

In another preferred embodiment, the mammal is human. Even more preferably, the tumour cells object of this invention overexpress the markers NF-kB, EGF, VEGF, TNF-$\alpha$, TGF-$\alpha$, TGF-$\beta$1, TGF-$\beta$2, TGF-$\beta$3, SPARC, MMP-3; MMP-7, MMP-9, MMP-11, MMP-13, MMP-14 and/or combinations thereof.

A third aspect of the invention relates to a composition, hereinafter composition of the invention, comprising a non-peptide NK1 receptor antagonist in a predetermined dose of the invention. In a preferred embodiment, the non-peptide NK1 receptor antagonist is selected from the list consisting of: Aprepitant, Vestipitant, Casopitant, Vofopitant, Ezlopitant, Lanepitant, LY-686017, L-733,060, L-732,138, L-703, 606, WIN 62,577, CP-122721, TAK-637, and R673, CP-100263, WIN 51708, CP-96345, L-760735, CP-122721, L-758298, L-741671, L-742694, CP-99994, T-2328, or any combinations thereof. In a more specific embodiment being especially preferred the antagonists selected from: Aprepitant, Vestipitant, Casopitant, Vofopitant, Ezlopitant and Lanepitant, or any combinations thereof. Even much more preferably, the non-peptide NK1 receptor antagonist is Aprepitant.

In another preferred embodiment of this aspect of the invention, the composition of the invention is a pharmaceutical composition. More preferably, the composition may further comprise a pharmaceutically acceptable carrier and/or excipients. Even more preferably, it additionally comprises at least one other active principle (active principle B). Preferably, the active principle B is selected from the list consisting of: Chlorambucil, Melphalan, Aldesleukin, 6-Mercaptopurine, 5-Fluorouracil, Ara-c, Bexarotene, Bleomycin, Capecitabine, Carboplatin, Cisplatin, Docetaxel, Doxorubicin, Epirubicin, Fludarabine, Irinotecan Methotrexate, Mitoxantrone, Oxaliplatin, Paclitaxel, Rituximab, Vinblastine, Etoposide, Teniposide, Vincristine, Vinorelbine, Imatinib, Erlotinib, Cetuximab, Trastuzumab, or any combinations thereof.

In another preferred embodiment of the present invention the duration of the treatment is between 7 and 90 days, even more preferably, it is of 7, 15, 30 or 90 days. Furthermore, both the non-peptide NK1 receptor antagonist in a predetermined dose of the invention, and the combined preparation and the composition of the invention, can be administered one or several times a day, for example, two, three, four or five times a day. Preferably the number of administrations shall be three times a day.

DETAILED DESCRIPTION OF THE INVENTION

The examples of the present invention demonstrate that the non-peptide NK1 receptor antagonists, used in suitable doses, alone or in combination with other anti-tumour and/or radiotherapy drugs, may inhibit the growth of cancerous tumours.

There was previously a dispute in terms of the effects of these antagonists, since, for example, in Mayordomo et al., (2012. *Journal of Cellular Physiology*, 227(4), 1358-1366) it indicates that none of the NK1 receptor antagonists used in clinical trials has shown good anti-tumour activity. In Lewis et al., (2013. *Anti-Cancer Drugs*, 24(4), 344-354), it shows that the use of Aprepitant at doses of 3 mg per kilogram of weight and day, does not produce reduction in the size of brain tumours in animal experimentation models.

The modifications produced in the microperitumoral environment in mammals, including humans, which are produced by means of treatment with at least one non-peptide NK1 receptor antagonist, in suitable doses, may be summarized in the modification of the immunophenotype of the cells that form said microenvironment, preferably, fibroblasts, inflammatory cells and vascular endothelial cells, preferably related to the synthesis of key molecules in tumour progression, such as, for example, MMPs, NF-KB, TGFβ and SPARC.

Another of the modifications of said microperitumoral environment, via treatment with non-peptide NK1 antagonists, used at suitable doses, relates to the inhibition of neoangiogenesis by means of inhibition of the proliferation of vascular endothelial cells, a determining factor for tumour progression. Therefore, the use of non-peptide NK1 receptor antagonists gives rise to modification in the cells forming the tumour microenvironment, cells of fibroblastic cell line (stroma), vascular endothelial cells (vessels) and cells involved in the inflammatory and immune response (which promote the growth and perpetuation of the tumours by means of the interaction between the stroma and cancer cells) said modifications being beneficial for cancer treatment. These changes in the tumour microenvironment are aimed at reducing tumour size or its complete elimination, as well as preventing the development and the progression thereof.

Therefore, for the purposes of the present invention the NK1 receptor antagonist used at predetermined doses alone, in combination with other NK1 receptor antagonists and/or other anti-tumour products and/or radiotherapy, has the capacity of modifying the peritumoral environment, as previously defined. Nevertheless, it is necessary to administer the antagonists at suitable doses, since even, as shown in example 13 of this specification, at predetermined doses (concentrations of the nanomolar range) the NK1 receptor antagonists, in certain tumour cell lines, induce an increase in proliferation of said cells.

Therefore, a first aspect of the present invention relates to the use of a non-peptide NK1 receptor antagonist at doses between 5 and 120 mg/kg of weight per day, hereinafter non-peptide NK1 receptor antagonist in a predetermined dose of the invention, in the preparation of a medicament for the treatment of cancer in a mammal. In a preferred embodiment of this aspect of the invention, the dose is between 8 and 100 mg/kg of weight per day. Even more preferably, the dose is even more preferably between 10-80 mg/kg of weight per day. In another even much more preferred embodiment, the dose is between 30 and 50 mg/kg of weight per day, and even much more preferably between 35 and 45 mg/kg of weight per day. In a particular embodiment, it is of approximately 40 mg/kg of weight per day. The NK1 antagonists may be administered one, two, three, four or more times a day, in a total daily amount as indicated above.

As used here "non-peptide NK1 receptor antagonist" means any substance of non-peptide nature with sufficient size and suitable formation to bond to the NK1 receptor and thus inhibit its normal functioning, including the fact of avoiding that the SP or other agonists of these receptors bond to said receptors. Preferably, in the present invention, the following commercial non-peptide NK1 receptor antagonists have been tested: L-733,060 ((2S,3S)-3-[(3,5-bis(Trifluoromethyl)phenyl)methoxy]-2-phenylpiperidine hydrochloride) (Sigma-Aldrich), L-732,138 (N-Acetyl-L-tryptophan 3,5-bis(trifluoromethyl)benzyl ester) (Sigma-Aldrich), L-703,606 (cis-2-(Diphenylmethyl)-N-[(2-iodophenyl)methyl]-1-azabicyclo[2.2.2]octan-3-amine oxalate salt) (Sigma-Aldrich), WIN 62,577 (Sigma-Aldrich), CP-122721 (Pfizer), Aprepitant or MK 869 or L-754030 (MSD), TAK-637 (Takeda/Abbot), Vestipitant or GW597599 (GSK), Casopitant or GW679769 (GSK) and R673 (Roche). CP-100263, WIN 51708, CP-96345, L-760735. Similarly, it is possible to use other non-peptide NK1 and SP receptor antagonist compounds such as: Vofopitant or GR-205171 (Pfizer), Ezlopitant or CJ-11974 (Pfizer), CP-122721 (Pfizer), L-758298 (MSD), L-741671, L-742694, CP-99994, Lanepitant or LY-303870, T-2328, LY-686017. The following compounds are preferred: Aprepitant or MK 869 or L-754030 (MSD), Vestipitant or GW597599 (GSK) and Casopitant or GW679769 (GSK).

Therefore, in another preferred embodiment, the non-peptide NK1 receptor antagonist is selected from the list consisting of: Aprepitant, Vestipitant, Casopitant, Vofopitant, Ezlopitant, Lanepitant, LY-686017, L-733,060, L-732,138, L-703,606, WIN 62,577, CP-122721, TAK-637, and R673, CP-100263, WIN 51708, CP-96345, L-760735, CP-122721, L-758298, L-741671, L-742694, CP-99994, T-2328, or any combinations thereof. In a more specific embodiment being especially preferred the antagonists selected from: Aprepitant, Vestipitant, Casopitant, Vofopitant, Ezlopitant and Lanepitant, or any combinations thereof. Even much more preferably, the non-peptide NK1 receptor antagonist is Aprepitant.

In another preferred embodiment of this aspect of the invention, the cancer is selected from the list comprising: gastric cancer, colon cancer, pancreatic cancer, breast cancer, ovarian cancer, endometrial cancer, choriocarcinoma, uterine cervical cancer, lung cancer, thyroid cancer, bladder cancer, prostate cancer, glial tumours of the central nervous system, sarcomas, melanomas, embryonal carcinoma and haematological malignancies. In another more preferred embodiment, the cancer presents with alteration of the peritumoral environment. In another more preferred embodiment, the cancer that presents with alteration of the peritumoral environment shows an increased synthesis of the markers selected from the list consisting of: NF-kB, EGF, VEGF, TNF-α, TGF-α, TGF-β1, TGF-β2, TGF-β3, SPARC, MMP-3; MMP-7, MMP-9, MMP-11, MMP-13, MMP-14 and/or combinations thereof.

In another preferred embodiment, the mammal is human. Even more preferably, the tumour cells treated with the object of the invention overexpress the markers NF-kB, EGF, VEGF, TNF-α, TGF-α, TGF-β1, TGF-β2, TGF-β3, SPARC, MMP-3; MMP-7, MMP-9, MMP-11, MMP-13, MMP-14 and/or any of the combinations thereof.

A second aspect of the invention relates to the use of a combined preparation comprising a non-peptide NK1 receptor antagonist in a predetermined dose of the invention, in combination with at least one active principle, hereinafter active principle B of the invention, which induces apoptosis in the tumour cells, in the preparation of a medicament for the treatment of cancer. In a preferred embodiment, the non-peptide NK1 receptor antagonists selected from the list consisting of: Aprepitant, Vestipitant, Casopitant, Vofopitant, Ezlopitant, Lanepitant, LY-686017, L-733,060, L-732,138, L-703,606, WIN 62,577, CP-122721, TAK-637, and R673, CP-100263, WIN 51708, CP-96345, L-760735, CP-122721, L-758298, L-741671, L-742694, CP-99994, T-2328, or any combinations thereof. In a more specific embodiment being especially preferred the antagonists selected from: Aprepitant, Vestipitant, Casopitant, Vofopitant, Ezlopitant and Lanepitant, or any combinations thereof.

Even much more preferably, the non-peptide NK1 receptor antagonist is Aprepitant. In another preferred embodiment of this aspect of the invention, the active principle which induces apoptosis in the tumour cells is selected from the list consisting of: Chlorambucil, Melphalan, Aldesleukin, 6-Mercaptopurine, 5-Fluorouracil, Ara-c, Bexarotene, Bleomycin, Capecitabine, Carboplatin, Cisplatin, Docetaxel, Doxorubicin, Epirubicin, Fludarabine, Irinotecan Methotrexate, Mitoxantrone, Oxaliplatin, Paclitaxel, Rituximab, Vinblastine, Etoposide, Teniposide, Vincristine, Vinorelbine, Imatinib, Erlotinib, Cetuximab, Trastuzumab, or any combinations thereof.

In another preferred embodiment of this aspect of the invention, the non-peptide NK1 receptor antagonist of the invention and the active principle B of the invention (active principle which induces apoptosis) is administered separately, jointly or sequentially, and may additionally be combined with at least one other anti-cancer agent selected from a chemotherapy agent or a radiotherapy agent.

Non-peptide NK1 receptor antagonists in a predetermined dose relates to doses between 5 and 120 mg/kg of weight per day, and preferably between 8 and 100 mg/kg of weight per day. Even more preferably, the dose is between 10-80 mg/kg of weight per day.

In another preferred embodiment of this aspect of the invention, the cancer is selected from the list comprising: gastric cancer, colon cancer, pancreatic cancer, breast cancer, ovarian cancer, endometrial cancer, choriocarcinoma, uterine cervical cancer, lung cancer, thyroid cancer, bladder cancer, prostate cancer, glial tumours of the central nervous system, sarcomas, melanomas, embryonal carcinoma and haematological malignancies. In another more preferred embodiment, the cancer presents with alteration of the peritumoral environment. In another more preferred embodiment, the cancer that presents with alteration of the peritumoral environment shows an increased synthesis of the following markers selected from the list comprising: NF-kB, EGF, VEGF, TNF-α, TGF-α, TGF-β1, TGF-β2, TGF-β3, SPARC, MMP-3; MMP-7, MMP-9, MMP-11, MMP-13, MMP-14 and/or combinations thereof.

In another preferred embodiment, the mammal is human. Even more preferably, the tumour cells treated with the object of the invention overexpress the markers NF-kB, EGF, VEGF, TNF-α, TGF-α, TGF-β1, TGF-β2, TGF-β3, SPARC, MMP-3; MMP-7, MMP-9, MMP-11, MMP-13, MMP-14 and/or any of the combinations thereof.

A third aspect of the invention relates to a composition, hereinafter composition of the invention, comprising a non-peptide NK1 receptor antagonist at a predetermined dose of the invention. In a preferred embodiment, the non-peptide NK1 receptor antagonist is selected from the list consisting of: Aprepitant, Vestipitant, Casopitant, Vofopitant, Ezlopitant, Lanepitant, LY-686017, L-733,060, L-732,138, L-703, 606, WIN 62,577, CP-122721, TAK-637, and R673, CP-100263, WIN 51708, CP-96345, L-760735, CP-122721, L-758298, L-741671, L-742694, CP-99994, T-2328, or any combinations thereof. In a more specific embodiment being especially preferred the antagonists selected from: Aprepitant, Vestipitant, Casopitant, Vofopitant, Ezlopitant and Lanepitant, or any combinations thereof. Even much more preferably, the non-peptide NK1 receptor antagonist is Aprepitant.

In another preferred embodiment of this aspect of the invention, the composition of the invention is a pharmaceutical composition. More preferably, the composition may further comprise a pharmaceutically acceptable carrier and/or excipients. Even more preferably, it additionally comprises at least one other active principle (active principle B). Preferably, the active principle B is selected from the list consisting of: Chlorambucil, Melphalan, Aldesleukin, 6-Mercaptopurine, 5-Fluorouracil, Ara-c, Bexarotene, Bleomycin, Capecitabine, Carboplatin, Cisplatin, Docetaxel, Doxorubicin, Epirubicin, Fludarabine, Irinotecan Methotrexate, Mitoxantrone, Oxaliplatin, Paclitaxel, Rituximab, Vinblastine, Etoposide, Teniposide, Vincristine, Vinorelbine, Imatinib, Erlotinib, Cetuximab, Trastuzumab, or any combinations thereof.

In another preferred embodiment it relates to the use of a pharmaceutical composition comprising a non-peptide NK1 receptor antagonist in the preparation of a medicament in the treatment of cancer, where the non-peptide NK1 receptor antagonist is found in the blood in a necessary concentration to reach serum concentrations equal to or greater than 100 nanomolar, Even more preferably, the non-peptide NK1 receptor antagonist is found in blood at a necessary concentration to reach serum concentrations equal to or greater than 1 micromolar.

It should be understood that the pharmaceutical composition or medicament comprising at least one non-peptide NK1 receptor antagonist at a predetermined dose, is presented in a pharmaceutically acceptable form to be administered to an individual directly, preferably by means of intravenous, oral, parenteral route, or by any other route. Intravenous administration relates directly to the application of the antagonist or of a pharmaceutical composition comprising it, directly in the patient's blood stream. Oral administration may involve the swallowing, so that the antagonist, as well as a pharmaceutical composition comprising it, enters in the gastrointestinal tract, or buccal or sublingual administration can be used by means of which the compound enters the bloodstream directly from the mouth. Parenteral administration relates to administration routes other than enteric, transdermal or by inhalation and is typically by injection or infusion. Parenteral administration includes injection or intravenous, intramuscular or subcutaneous infusion.

The term "medicament" or "pharmaceutical composition", as used in this specification, makes reference to any substance used to prevent, diagnose, relieve, treat or cure diseases in humans and animals. In the context of the present invention, the disease is cancer, preferably of epithelial cell line (cancers), glial cell line of the central nervous system, mesenchymal cell line (sarcomas), of melatonic cell line (melanoma), of embryonic origin (e.g. neuroblastoma) or of haemato-lymphoid cell line (lymphomas and leukaemias).

It should be emphasized that the term "combined preparation" or also called "juxtaposition", in this specification, means that the components of the combined preparation do not need to be present as a bond, e.g. in a composition, to be able to be found available for their separate or sequential application. In this way, the expression "juxtaposed" means that a true combination is not necessary, in light of the physical separation of the components.

As used here, the term "active principle", "active substance", "pharmaceutically active substance", "active ingredient" or "pharmaceutically active ingredient" means any component that potentially provides a pharmacological activity or another different effect in the diagnosis, cure, mitigation, treatment or prevention of a disease or which affects the structure of the body of humans or other animals. The term includes those components which promote a chemical change in preparation of the drug and are present in the same in a provided modified form which provides the specific activity or the effect.

The treatment described in the present invention is useful for patients affected by cancer, in asymptomatic or symptomatic condition, in neoadjuvant therapy (treatment before surgery), in adjuvant therapy (complementary treatment after surgery, where there is no detectable macroscopic tumour) and in treatment of the disease in metastatic stage.

A person skilled in the art shall adapt the composition depending on the particular administration route. In the case of administering a purified antibody, oral administration is the preferred method and it is preferably achieved through solid dosing forms, which includes capsules, tablets, pills, powders and granules, among others, or by liquid dosing forms. The preparations of the modifying agent of the peritumoral environment for parenteral administration preferably include aqueous solutions or sterile non aqueous solutions, suspensions or emulsions, among others. The term "pharmaceutically acceptable carrier" relates to a carrier that must be approved by a regulatory agency of the federal government or state government or listed in the United States Pharmacopoeia or the European Pharmacopoeia, or another pharmacopeia generally recognised for its use in animals, and more specifically in humans. Likewise, the suitable pharmaceutically acceptable excipients shall vary depending on the particular dosing form selected. Furthermore, the suitable pharmaceutically acceptable excipients may be selected for a particular function which they may have in the composition. For example, certain pharmaceutically acceptable excipients may be selected for their capacity to facilitate the production of uniform dosing forms. Certain pharmaceutically acceptable excipients may be selected for their capacity to facilitate the production of stable dosing forms. Certain pharmaceutically acceptable excipients may be selected for their capacity to facilitate the transport of the compound or compounds of the invention once administered to the patient from an organ or part of the body to another organ or part of the body. Certain pharmaceutically acceptable excipients may be selected for their capacity to improve acceptance by the patient. The suitable pharmaceutically acceptable excipients include the following types of excipients, without excluding others known in the state of the art: diluents, fillers, binding agents, disintegrants, lubricants, slip agents, granulation agents, coating agents, hydrating agents, solvents, co-solvents, suspension agents, emulsifiers, sweeteners, flavourings, flavour-masking agents, colouring agents, anti-caking agents, wetting agents, chelating agents, agents to increase viscosity, antioxidants, preservatives, stabilizers, surfactants and buffering agents. Persons skilled in the art will appreciate that certain pharmaceutically acceptable excipients may perform more than one function and may perform alternative functions depending on the amount of excipient and on the other ingredients present in the formulation. Specialists have the knowledge and ability in the technique that allows them to select suitable pharmaceutically acceptable excipients in the appropriate amounts for use in the invention. There are also several available resources for persons skilled in the art that describe pharmaceutically acceptable excipients and may be useful in the selection of suitable pharmaceutically acceptable excipients. The examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The dosing of the active ingredient, in the present invention, of the non-peptide NK1 receptor antagonist, shall be selected depending on the desired therapeutic effect, the administration route and treatment duration. The administration does and the frequency shall depend on the size, age and conditions of general health of the individual, bearing in mind the possibility of secondary effects The administration shall also depend on the simultaneous treatment with other drugs and the tolerance of each individual to the drug administered. Persons skilled in the art can establish the appropriate dose using standard procedures. It is understood that the dose must be the effective quantity of the active principle, modulating agent of the peritumoral environment, preferably non-peptide NK1 antagonist, in the sense that the treatment has at least the same or better effect that current therapies in these patients.

"Cancer" is understood as a malignant tumour of potential unlimited growth which locally expands due to invasion and systemically by metastasis. In the present invention, the non-peptide NK1 receptor antagonist is administered to individuals with a cancer.

Unless defined otherwise, all the technical and scientific terms have the same meaning as those commonly understood by a person skilled in the art in the field of the invention. Similar and equivalent methods and materials to those described here may be used in the practice of the present invention. Throughout the description and the claims, the word "comprises" and its variants, are not limiting in nature and therefore do not aim to exclude other technical characteristics, additives, components or steps. In contrast, the word "consists" and its variants do have a limiting character, exclusively referring to the technical characteristics, additive, components or steps that accompany them. For persons skilled in the art, other objectives, advantages and characteristics of the invention will be inferred in part from the description and in part from the practice of the invention.

EXAMPLES OF THE INVENTION

Below, examples are shown by way of illustration, without aiming for them to be limitative of the present invention, where the advantages of the invention are disclosed.

Example 1. Treatment with Non-Peptide NK1 Receptor Antagonists, at Doses Between 10 and 80 mg Per Kilogram of Weight and Day, Reduces the Size of Cancerous Tumours of Epithelial Cell Line (Cancers) in Mammals To verify that the administration of the antagonists not of the NK1 receptors, at doses between 10 and 80 mg per kilogram of weight and day, reduces the sizes of epithelial cell line tumours (cancers) in mammals, tumour cells were implanted in mice and were later treated with non-peptide NK1 receptor antagonists.

Immunocompromised female mice, 5-6 weeks of age were used, nu/nu Balb/c nude mice, provided by Harlan Iberica Barcelona (Spain). They were kept at 24° C. and in sterile conditions with food and water "ad libitum". They were injected with $2 \times 10^7$ tumour cells, corresponding to cancer (human lung cancer, reference HCC-44 supplied by DSMZ) in 200 µl of PBS subcutaneous route. The tumour size was measured and the mice were evaluated for their state of health and weight daily. The mice were randomized in nine groups when the tumours reached a volume of 75 mm$^3$. One of the groups was treated with 200 µl of placebo (control group) and the eight remaining groups with doses of 10 (group 1), 20 (group 2), 30 (group 3), 40 (group 4), 50 (group 5), 60 (group 6), 70 (group 7) and 80 (group 8) mg per kilogram of weight and day of the NK1 receptor antagonist Aprepitant. 3 animals were treated per group, during 28 days. All the mice were sacrificed at the end of the experiment. Table 1 shows the tumour size (in cubic millimeters±standard deviation) after 7, 14, 21 and 28 days, of treatment, respectively with each one of the doses used.

TABLE 1

Tumour size of the tumours provoked in an in vivo mouse model. Mean volume of the tumour in the control mice (untreated) or in the mice after treatment with the non-peptide NK1 receptor antagonist (Aprepitant).

| Lung cancer cell line reference HCC-44. | 7 days | 14 days | 21 days | 28 days |
|---|---|---|---|---|
| Control | 230 ± 6 | 270 ± 5 | 310 ± 6 | 340 ± 8 |
| Group 1 (10 mg/kg/day) | 210 ± 2 | 190 ± 4 | 165 ± 6 | 135 ± 3 |
| Group 2 (20 mg/kg/day) | 205 ± 8 | 170 ± 3 | 145 ± 4 | 110 ± 4 |
| Group 3 (30 mg/kg/day) | 185 ± 4 | 150 ± 6 | 135 ± 5 | 105 ± 2 |
| Group 4 (40 mg/kg/day) | 155 ± 5 | 130 ± 4 | 120 ± 4 | 95 ± 4 |
| Group 5 (50 mg/kg/day) | 130 ± 4 | 115 ± 7 | 105 ± 6 | 85 ± 6 |
| Group 6 (60 mg/kg/day) | 110 ± 3 | 95 ± 8 | 80 ± 7 | 65 ± 4 |
| Group 7 (70 mg/kg/day) | 95 ± 4 | 80 ± 6 | 65 ± 8 | 40 ± 7 |
| Group 8 (80 mg/kg/day) | 70 ± 4 | 55 ± 7 | 40 ± 6 | 25 ± 5 |

Example 2. Treatment with Non-Peptide NK1 Receptor Antagonists, at Doses Between 10 and 80 mg Per Kilogram of Weight and Day, Reduces the Size of Cancerous Tumours of Glial Cell Line (e.g. Astrocytomas) of the Central Nervous System in Mammals To verify that the administration of the antagonists not of the NK1 receptors, at doses between 10 and 80 mg per kilogram of weight and day, reduces the sizes of glial cell line tumours of the nervous system in mammals, tumour cells were implanted in mice and were later treated with non-peptide NK1 receptor antagonists.

Immunocompromised female mice, 5-6 weeks of age were used, in the same conditions as explained in example 1. They were injected with $2 \times 10^7$ tumour cells, corresponding to a glial cell line tumour of the central nervous system human (human glioma; reference GAMG; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with 200 µl of placebo (control group) and the eight remaining groups with doses of 10 (group 1), 20 (group 2), 30 (group 3), 40 (group 4), 50 (group 5), 60 (group 6), 70 (group 7) and 80 (group 8) mg per kilogram of weight and day of the NK1 receptor antagonist Aprepitant. 3 animals were treated per group, during 28 days. All the mice were sacrificed at the end of the experiment. Table 2 shows the tumour size (in cubic millimeters±standard deviation) after 7, 14, 21 and 28 days, of treatment, respectively with each one of the doses used.

TABLE 2

Tumour size of the tumours provoked in an in vivo mouse model. Mean volume of the tumour in the control mice (untreated) or in the mice after treatment with the non-peptide NK1 receptor antagonist (Aprepitant).

| Glioma cell line, reference GAMG | 7 days | 14 days | 21 days | 28 days |
|---|---|---|---|---|
| Control | 210 ± 4 | 245 ± 6 | 290 ± 5 | 315 ± 6 |
| Group 1 (10 mg/kg/day) | 205 ± 3 | 185 ± 6 | 170 ± 7 | 155 ± 4 |
| Group 2 (20 mg/kg/day) | 190 ± 4 | 160 ± 7 | 150 ± 6 | 125 ± 5 |
| Group 3 (30 mg/kg/day) | 160 ± 4 | 145 ± 7 | 120 ± 6 | 105 ± 4 |
| Group 4 (40 mg/kg/day) | 155 ± 6 | 125 ± 5 | 110 ± 5 | 90 ± 9 |
| Group 5 (50 mg/kg/day) | 125 ± 5 | 110 ± 5 | 100 ± 5 | 80 ± 8 |
| Group 6 (60 mg/kg/day) | 95 ± 5 | 85 ± 6 | 60 ± 6 | 50 ± 7 |
| Group 7 (70 mg/kg/day) | 75 ± 6 | 60 ± 5 | 55 ± 5 | 35 ± 8 |
| Group 8 (80 mg/kg/day) | 60 ± 3 | 45 ± 6 | 25 ± 7 | 15 ± 10 |

Example 3. Treatment with Non-Peptide NK1 Receptor Antagonists, at Doses Between 10 and 80 mg Per Kilogram of Weight and Day, Reduces the Size of Cancerous Tumours of Mesenchymal Cell Line (Sarcomas) in Mammals To verify that the administration of the antagonists not of the NK1 receptors, at doses between 10 and 80 mg per kilogram of weight and day, reduces the sizes of glial cell line tumours of the nervous system in mammals, tumour cells were implanted in mice and were later treated with non-peptide NK1 receptor antagonists.

Immunocompromised female mice, 5-6 weeks of age were used, in the same conditions as explained in example 1. They were injected with $2 \times 10^7$ tumour cells, corresponding to a mesenchymal cell line tumour (human fibrosarcoma; reference HT-1080; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with 200 µl of placebo (control group) and the eight remaining groups with doses of 10 (group 1), 20 (group 2), 30 (group 3), 40 (group 4), 50 (group 5), 60 (group 6), 70 (group 7) and 80 (group 8) mg per kilogram of weight and day of the NK1 receptor antagonist Aprepitant. 3 animals were treated per group, during 28 days. All the mice were sacrificed at the end of the experiment. Table 3 shows the tumour size (in cubic millimeters±standard deviation) after 7, 14, 21 and 28 days, of treatment, respectively with each one of the doses used.

TABLE 3

Tumour size of the tumours provoked in an in vivo mouse model. Mean volume of the tumour in the control mice (untreated) or in the mice after treatment with the non-peptide NK1 receptor antagonist (Aprepitant).

| Fibrosarcoma cell line, reference HT-1080. | 7 days | 14 days | 21 days | 28 days |
|---|---|---|---|---|
| Control | 255 ± 5 | 270 ± 3 | 310 ± 4 | 340 ± 7 |
| Group 1 (10 mg/kg/day) | 220 ± 4 | 205 ± 4 | 195 ± 6 | 170 ± 6 |
| Group 2 (20 mg/kg/day) | 195 ± 5 | 180 ± 5 | 165 ± 7 | 150 ± 7 |
| Group 3 (30 mg/kg/day) | 175 ± 5 | 155 ± 6 | 135 ± 5 | 140 ± 4 |
| Group 4 (40 mg/kg/day) | 160 ± 4 | 150 ± 3 | 120 ± 5 | 110 ± 6 |
| Group 5 (50 mg/kg/day) | 145 ± 5 | 135 ± 7 | 100 ± 3 | 100 ± 7 |
| Group 6 (60 mg/kg/day) | 135 ± 7 | 120 ± 6 | 90 ± 8 | 85 ± 4 |
| Group 7 (70 mg/kg/day) | 120 ± 8 | 100 ± 4 | 85 ± 6 | 80 ± 7 |
| Group 8 (80 mg/kg/day) | 100 ± 4 | 90 ± 8 | 70 ± 8 | 65 ± 9 |

Example 4. Treatment with Non-Peptide NK1 Receptor Antagonists, at Doses Between 10 and 80 mg Per Kilogram of Weight and Day, Reduces the Size of Cancerous Tumours of Haematological Cell Line (Leukaemias/Lymphomas) in Mammals To verify that the administration of the antagonists not of the NK1 receptors, at doses between 10 and 80 mg per kilogram of weight and day, reduces the sizes of glial cell line tumours of the nervous system in mammals, tumour cells were implanted in mice and were later treated with non-peptide NK1 receptor antagonists.

Immunocompromised female mice, 5-6 weeks of age were used, in the same conditions as explained in example 1. They were injected with $2 \times 10^7$ tumour cells, corresponding to a haematological cell line tumour (human lymphoma; reference BC-1; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with 200 µl of placebo (control group) and the eight remaining groups with doses of 10 (group 1), 20 (group 2), 30 (group 3), 40 (group 4), 50 (group 5), 60 (group 6), 70 (group 7) and 80 (group 8) mg per kilogram of weight and day of the NK1 receptor antagonist Aprepitant. 3 animals were treated per group, during 28 days. All the mice were sacrificed at the end of the experiment. Table 4 shows the tumour size (in cubic millimeters±standard deviation) after 7, 14, 21 and 28 days, of treatment, respectively with each one of the doses used.

TABLE 4

Tumour size of the tumours provoked in an in vivo mouse model. Mean volume of the tumour in the control mice (untreated) or in the mice after treatment with the non-peptide NK1 receptor antagonist (Aprepitant).

| Lymphoma cell line, reference BC-1. | 7 days | 14 days | 21 days | 28 days |
| --- | --- | --- | --- | --- |
| Control | 230 ± 6 | 210 ± 5 | 195 ± 6 | 340 ± 7 |
| Group 1 (10 mg/kg/day) | 210 ± 3 | 195 ± 6 | 175 ± 7 | 170 ± 6 |
| Group 2 (20 mg/kg/day) | 195 ± 6 | 175 ± 7 | 160 ± 6 | 150 ± 7 |
| Group 3 (30 mg/kg/day) | 180 ± 7 | 155 ± 4 | 145 ± 8 | 140 ± 4 |
| Group 4 (40 mg/kg/day) | 165 ± 8 | 165 ± 6 | 130 ± 5 | 110 ± 6 |
| Group 5 (50 mg/kg/day) | 150 ± 5 | 145 ± 7 | 120 ± 6 | 100 ± 7 |
| Group 6 (60 mg/kg/day) | 130 ± 6 | 130 ± 8 | 100 ± 7 | 85 ± 4 |
| Group 7 (70 mg/kg/day) | 110 ± 4 | 105 ± 4 | 80 ± 5 | 80 ± 7 |
| Group 8 (80 mg/kg/day) | 95 ± 6 | 85 ± 6 | 65 ± 3 | 65 ± 9 |

Example 5. Treatment with Non-Peptide NK1 Receptor Antagonists, at Doses Between 10 and 80 mg Per Kilogram of Weight and Day, Reduces the Size of Cancerous Tumours of Melanoma Cell Line (Melanomas) in Mammals To verify that the administration of the antagonists not of the NK1 receptors, at doses between 10 and 80 mg per kilogram of weight and day, reduces the sizes of glial cell line tumours of the nervous system in mammals, tumour cells were implanted in mice and were later treated with non-peptide NK1 receptor antagonists.

Immunocompromised female mice, 5-6 weeks of age were used, in the same conditions as explained in example 1. They were injected with $2 \times 10^7$ tumour cells, corresponding to a melanoma cell line tumour (human melanoma; reference MEL-HO; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with 200 µl of placebo (control group) and the eight remaining groups with doses of 10 (group 1), 20 (group 2), 30 (group 3), 40 (group 4), 50 (group 5), 60 (group 6), 70 (group 7) and 80 (group 8) mg per kilogram of weight and day of the NK1 receptor antagonist Aprepitant. 3 animals were treated per group, during 28 days. All the mice were sacrificed at the end of the experiment. Table 5 shows the tumour size (in cubic millimeters±standard deviation) after 7, 14, 21 and 28 days, of treatment, respectively with each one of the doses used.

TABLE 5

Tumour size of the tumours provoked in an in vivo mouse model. Mean volume of the tumour in the control mice (untreated) or in the mice after treatment with the non-peptide NK1 receptor antagonist (Aprepitant).

| Melanoma cell line, reference MEL-HO. | 7 days | 14 days | 21 days | 28 days |
| --- | --- | --- | --- | --- |
| Control | 250 ± 6 | 230 ± 6 | 205 ± 7 | 340 ± 7 |
| Group 1 (10 mg/kg/day) | 235 ± 3 | 215 ± 4 | 190 ± 4 | 170 ± 6 |
| Group 2 (20 mg/kg/day) | 210 ± 6 | 200 ± 5 | 175 ± 5 | 150 ± 7 |
| Group 3 (30 mg/kg/day) | 195 ± 7 | 185 ± 6 | 160 ± 6 | 140 ± 4 |
| Group 4 (40 mg/kg/day) | 175 ± 8 | 160 ± 8 | 140 ± 4 | 110 ± 6 |
| Group 5 (50 mg/kg/day) | 160 ± 5 | 150 ± 4 | 125 ± 5 | 100 ± 7 |
| Group 6 (60 mg/kg/day) | 145 ± 6 | 135 ± 5 | 115 ± 6 | 85 ± 4 |
| Group 7 (70 mg/kg/day) | 125 ± 4 | 105 ± 6 | 90 ± 4 | 80 ± 7 |
| Group 8 (80 mg/kg/day) | 100 ± 6 | 95 ± 7 | 65 ± 7 | 65 ± 9 |

Example 6. Treatment with Non-Peptide NK1 Receptor Antagonists, at Doses Between 10 and 80 mg Per Kilogram of Weight and Day, Reduces the Size of Cancerous Tumours of Embryonic Character (e.g. Neuroblastoma) in Mammals To verify that the administration of the antagonists not of the NK1 receptors, at doses between 10 and 80 mg per kilogram of weight and day, reduces the sizes of glial cell line tumours of the nervous system in mammals, tumour cells were implanted in mice and were later treated with non-peptide NK1 receptor antagonists.

Immunocompromised female mice, 5-6 weeks of age were used, in the same conditions as explained in example 1. They were injected with $2 \times 10^7$ tumour cells, corresponding to an embryonic tumour (human neuroblastoma; reference KELLY; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with 200 µl of placebo (control group) and the eight remaining groups with doses of 10 (group 1), 20 (group 2), 30 (group 3), 40 (group 4), 50 (group 5), 60 (group 6), 70 (group 7) and 80 (group 8) mg per kilogram of weight and day of the NK1 receptor antagonist Aprepitant. 3 animals were treated per group, during 28 days. All the mice were sacrificed at the end of the experiment. Table 6 shows the tumour size (in cubic millimeters±standard deviation) after 7, 14, 21 and 28 days, of treatment, respectively with each one of the doses used.

TABLE 6

Tumour size of the tumours provoked in an in vivo mouse model. Mean volume of the tumour in the control mice (untreated) or in the mice after treatment with the non-peptide NK1 receptor antagonist (Aprepitant).

| Cell line of neuroblastoma reference KELLY. | 7 days | 14 days | 21 days | 28 days |
|---|---|---|---|---|
| Control | 195 ± 5 | 170 ± 5 | 155 ± 6 | 135 ± 6 |
| Group 1 (10 mg/kg/day) | 180 ± 4 | 165 ± 6 | 140 ± 5 | 120 ± 2 |
| Group 2 (20 mg/kg/day) | 175 ± 7 | 155 ± 7 | 130 ± 4 | 105 ± 4 |
| Group 3 (30 mg/kg/day) | 160 ± 3 | 145 ± 3 | 115 ± 3 | 90 ± 6 |
| Group 4 (40 mg/kg/day) | 155 ± 6 | 130 ± 6 | 105 ± 7 | 75 ± 8 |
| Group 5 (50 mg/kg/day) | 140 ± 4 | 110 ± 5 | 95 ± 7 | 60 ± 5 |
| Group 6 (60 mg/kg/day) | 130 ± 5 | 115 ± 7 | 85 ± 3 | 55 ± 9 |
| Group 7 (70 mg/kg/day) | 120 ± 6 | 95 ± 8 | 65 ± 6 | 40 ± 5 |
| Group 8 (80 mg/kg/day) | 105 ± 7 | 85 ± 6 | 45 ± 5 | 25 ± 6 |

Example 7. Treatment with Non-Peptide NK1 Receptor Antagonists at Doses Between 1 and 10 mg Per Kilogram of Weight and Day, in Combination with Another Anti-Tumour Drug, Reduces the Size of Cancerous Tumours of Epithelial Cell Line (Cancers) in Mammals To verify that the administration of the antagonists not of the NK1 receptors, at doses between 1 and 10 mg per kilogram of weight and day, in combination with other anti-tumour agents, reduces the sizes of epithelial cell line tumours (cancers) in mammals, tumour cells were implanted in mice and were later treated with chemotherapeutic agents, alone and in combination with non-peptide NK1 receptor antagonists.

Immunocompromised female mice, 5-6 weeks of age were used, in the same conditions as explained in example 1. They were injected with $2 \times 10^7$ tumour cells, corresponding to an epithelial cell line tumour (human lung cancer; reference HCC-44; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with Cisplatin at 8 mg per kilogram of weight at single doses on days 1 and 7 of the experiment (control group) and the eight remaining groups with the same treatment as the control group and the doses of 1 (group 1), 3 (group 2), 5 (group 3), 6 (group 4), 7 (group 5), 8 (group 6), 9 (group 7) and 10 (group 8) mg per kilogram of weight and day, of the NK1 receptor antagonist Aprepitant. 3 animals were treated per group, during 14 days. All the mice were sacrificed at the end of the experiment. Table 7 shows the tumour size (in cubic millimeters±standard deviation) after 7 and 14 days of treatment, with each one of the doses used.

TABLE 7

Tumour size of the tumours provoked in an in vivo mouse model. Mean volume of the tumour in the control mice (untreated) or in the mice after treatment with the non-peptide NK1 receptor antagonist (Aprepitant).

| Human lung cancer cell line, reference HCC-44. | 7 days | 14 days |
|---|---|---|
| Control. Cisplatin alone. | 105 ± 4 | 70 ± 7 |
| Group 1. Cisplatin + Aprepitant 1 mg/kg/day | 85 ± 6 | 55 ± 6 |
| Group 2. Cisplatin + Aprepitant 3 mg/kg/day | 70 ± 7 | 45 ± 7 |
| Group 3. Cisplatin + Aprepitant 5 mg/kg/day | 60 ± 8 | 30 ± 4 |
| Group 4. Cisplatin + Aprepitant 6 mg/kg/day | 55 ± 4 | 25 ± 6 |
| Group 5. Cisplatin + Aprepitant 7 mg/kg/day | 40 ± 3 | 10 ± 3 |
| Group 6. Cisplatin + Aprepitant 8 mg/kg/day | 35 ± 7 | 5 ± 2 |
| Group 7. Cisplatin + Aprepitant 9 mg/kg/day | 20 ± 6 | 0 ± 0 |
| Group 8. Cisplatin + Aprepitant 10 mg/kg/day | 10 ± 8 | 0 ± 0 |

Example 8. Treatment with Non-Peptide NK1 Receptor Antagonists at Doses Between 1 and 10 mg Per Kilogram of Weight and Day, in Combination with Another Anti-Tumour Drug, Reduces the Size of Cancerous Tumours of Glial Cell Line of the Nervous System (Gliomas) in Mammals To verify that the administration of the antagonists not of the NK1 receptors, at doses between 1 and 10 mg per kilogram of weight and day, in combination with other anti-tumour agents, reduces the sizes of glial cell line tumours (gliomas) of the nervous system in mammals, tumour cells were implanted in mice and were later treated with chemotherapeutic agents, alone and in combination with non-peptide NK1 receptor antagonists.

Immunocompromised female mice, 5-6 weeks of age were used, in the same conditions as explained in example 1. They were injected with $2 \times 10^7$ tumour cells, corresponding to a glial cell line tumour of the nervous system (human glioma; reference GAMG; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with two single doses of Cisplatin, of 8 mg per kilogram of weight, on days 1 and 7 of the experiment (control group). The eight remaining groups were treated with the same treatment as the control group and the doses of 1 (group 1), 3 (group 2), 5 (group 3), 6 (group 4), 7 (group 5), 8 (group 6), 9 (group 7) and 10 (group 8) mg per kilogram of weight and day, of the NK1 receptor antagonist Aprepitant. 3 animals were treated per group, during 14 days. All the mice were sacrificed at the end of the experiment. Table 8 shows the tumour size (in cubic millimeters±standard deviation) after 7 and 14 days of treatment, with each one of the doses used.

TABLE 8

Tumour size of the tumours provoked in an in vivo mouse model. Mean volume of the tumour in the control mice (untreated) or in the mice after treatment with the non peptide NK1 receptor antagonist (Aprepitant).

| Human glioma cell line, reference GAMG | 7 days | 14 days |
|---|---|---|
| Control. Cisplatin alone. | 115 ± 7 | 85 ± 6 |
| Group 1. Cisplatin + Aprepitant 1 mg/kg/day | 90 ± 5 | 60 ± 5 |
| Group 2. Cisplatin + Aprepitant 3 mg/kg/day | 80 ± 3 | 55 ± 4 |
| Group 3. Cisplatin + Aprepitant 5 mg/kg/day | 65 ± 2 | 40 ± 4 |
| Group 4. Cisplatin + Aprepitant 6 mg/kg/day | 60 ± 2 | 35 ± 3 |
| Group 5. Cisplatin + Aprepitant 7 mg/kg/day | 45 ± 4 | 20 ± 4 |
| Group 6. Cisplatin + Aprepitant 8 mg/kg/day | 30 ± 3 | 15 ± 3 |
| Group 7. Cisplatin + Aprepitant 9 mg/kg/day | 25 ± 2 | 10 ± 2 |
| Group 8. Cisplatin + Aprepitant 10 mg/kg/day | 5 ± 1 | 0 ± 0 |

Example 9. Treatment with Non-Peptide NK1 Receptor Antagonists at Doses Between 1 and 10 mg Per Kilogram of Weight and Day, in Combination with Another Anti-Tumour Drug, Reduces the Size of Cancerous Tumours of Mesenchymal Cell Line (Sarcomas) in Mammals To verify that the administration of the antagonists not of the NK1 receptors, at doses between 1 and 10 mg per kilogram of weight and day, in combination with other anti-tumour agents, reduces the sizes of mesenchymal cell line tumours (sarcomas) in mammals, tumour cells were implanted in mice and were later treated with chemotherapeutic agents, alone and in combination with non-peptide NK1 receptor antagonists.

Immunocompromised female mice, 5-6 weeks of age were used, in the same conditions as explained in example 1. They were injected with $2\times10^7$ tumour cells, corresponding to a mesenchymal cell line tumour (human fibrosarcoma; reference HT-1080; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with two single doses of Cisplatin, of 8 mg per kilogram of weight, on days 1 and 7 of the experiment (control group). The eight remaining groups were treated with the same treatment as the control group and the doses of 1 (group 1), 3 (group 2), 5 (group 3), 6 (group 4), 7 (group 5), 8 (group 6), 9 (group 7) and 10 (group 8) mg per kilogram of weight and day, of the NK1 receptor antagonist Aprepitant. 3 animals were treated per group, during 14 days. All the mice were sacrificed at the end of the experiment. Table 9 shows the tumour size (in cubic millimeters±standard deviation) after 7 and 14 days of treatment, with each one of the doses used.

TABLE 9

Tumour size of the tumours provoked in an in vivo mouse model. Mean volume of the tumour in the control mice (untreated) or in the mice after treatment with the non-peptide NK1 receptor antagonist (Aprepitant).

| Human fibrosarcoma cell line, reference HT-1080. | 7 days | 14 days |
|---|---|---|
| Control. Cisplatin alone. | 95 ± 5 | 65 ± 5 |
| Group 1. Cisplatin + Aprepitant 1 mg/kg/day | 80 ± 6 | 50 ± 7 |
| Group 2. Cisplatin + Aprepitant 3 mg/kg/day | 70 ± 7 | 35 ± 4 |
| Group 3. Cisplatin + Aprepitant 5 mg/kg/day | 55 ± 3 | 20 ± 3 |
| Group 4. Cisplatin + Aprepitant 6 mg/kg/day | 40 ± 3 | 15 ± 4 |
| Group 5. Cisplatin + Aprepitant 7 mg/kg/day | 25 ± 5 | 10 ± 5 |
| Group 6. Cisplatin + Aprepitant 8 mg/kg/day | 15 ± 2 | 5 ± 2 |
| Group 7. Cisplatin + Aprepitant 9 mg/kg/day | 10 ± 1 | 0 ± 0 |
| Group 8. Cisplatin + Aprepitant 10 mg/kg/day | 5 ± 2 | 0 ± 0 |

Example 10. Treatment with Non-Peptide NK1 Receptor Antagonists at Doses Between 1 and 10 mg Per Kilogram of Weight and Day, in Combination with Another Anti-Tumour Drug, Reduces the Size of Cancerous Tumours of Melanoma Cell Line (Melanomas) in Mammals To verify that the administration of the antagonists not of the NK1 receptors, at doses between 1 and 10 mg per kilogram of weight and day, in combination with other anti-tumour agents, reduces the sizes of melanoma cell line tumours (melanomas) in mammals, tumour cells were implanted in mice and were later treated with chemotherapeutic agents, alone and in combination with non-peptide NK1 receptor antagonists.

Immunocompromised female mice, 5-6 weeks of age were used, in the same conditions as explained in example 1. They were injected with $2\times10^7$ tumour cells, corresponding to a melanoma cell line tumour (human melanoma; reference MEL-HO; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with two single doses of Cisplatin, of 8 mg per kilogram of weight, on days 1 and 7 of the experiment (control group). The eight remaining groups were treated with the same treatment as the control group and the doses of 1 (group 1), 3 (group 2), 5 (group 3), 6 (group 4), 7 (group 5), 8 (group 6), 9 (group 7) and 10 (group 8) mg per kilogram of weight and day, of the NK1 receptor antagonist Aprepitant. 3 animals were treated per group, during 14 days. All the mice were sacrificed at the end of the experiment. Table 10 shows the tumour size (in cubic millimeters±standard deviation) after 7 and 14 days of treatment, with each one of the doses used.

TABLE 10

Tumour size of the tumours provoked in an in vivo mouse model. Mean volume of the tumour in the control mice (untreated) or in the mice after treatment with the non-peptide NK1 receptor antagonist (Aprepitant).

| Human melanoma cell line, reference MEL-HO. | 7 days | 14 days |
|---|---|---|
| Control. Cisplatin alone. | 105 ± 6 | 75 ± 6 |
| Group 1. Cisplatin + Aprepitant 1 mg/kg/day | 100 ± 7 | 55 ± 8 |
| Group 2. Cisplatin + Aprepitant 3 mg/kg/day | 95 ± 8 | 30 ± 8 |
| Group 3. Cisplatin + Aprepitant 5 mg/kg/day | 80 ± 5 | 25 ± 6 |
| Group 4. Cisplatin + Aprepitant 6 mg/kg/day | 65 ± 4 | 10 ± 7 |
| Group 5. Cisplatin + Aprepitant 7 mg/kg/day | 55 ± 3 | 15 ± 4 |
| Group 6. Cisplatin + Aprepitant 8 mg/kg/day | 40 ± 3 | 5 ± 3 |
| Group 7. Cisplatin + Aprepitant 9 mg/kg/day | 30 ± 2 | 0 ± 0 |
| Group 8. Cisplatin + Aprepitant 10 mg/kg/day | 25 ± 2 | 0 ± 0 |

Example 11. Treatment with Non-Peptide NK1 Receptor Antagonists at Doses Between 1 and 10 mg Per Kilogram of Weight and Day, in Combination with Another Anti-Tumour Drug, Reduces the Size of Cancerous Tumours of Embryonic Character (e.g. Neuroblastoma) in Mammals To verify that the administration of the antagonists not of the NK1 receptors, at doses between 1 and 10 mg per kilogram of weight and day, in combination with other anti-tumour agents, reduces the sizes of tumours of embryonic character (e.g. neuroblastoma) in mammals, tumour cells were implanted in mice and were later treated with chemotherapeutic agents, alone and in combination with non-peptide NK1 receptor antagonists.

Immunocompromised female mice, 5-6 weeks of age were used, in the same conditions as explained in example 1. They were injected with $2\times10^7$ tumour cells, corresponding to an embryonic tumour (human neuroblastoma; reference KELLY; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with two single doses of Cisplatin, of 8 mg per kilogram of weight, on days 1 and 7 of the experiment (control group). The eight remaining groups were treated with the same treatment as the control group and the doses of 1 (group 1), 3 (group 2), 5 (group 3), 6 (group 4), 7 (group 5), 8 (group 6), 9 (group 7) and 10 (group 8) mg per kilogram of weight and day, of the NK1 receptor antagonist Aprepitant. 3 animals were treated per group, during 14 days. All the mice were sacrified at the end of the experiment. Table 11 shows the tumour size (in cubic millimeters±standard deviation) after 7 and 14 days of treatment, with each one of the doses used.

TABLE 11

Tumour size of the tumours provoked in an in vivo mouse model. Mean volume of the tumour in the control mice (untreated) or in the mice after treatment with the non-peptide NK1 receptor antagonist (Aprepitant).

| Human neuroblastoma cell line, reference KELLY. | 7 days | 14 days |
|---|---|---|
| Control. Cisplatin alone. | 95 ± 8 | 60 ± 8 |
| Group 1. Cisplatin + Aprepitant 1 mg/kg/day | 80 ± 8 | 50 ± 6 |
| Group 2. Cisplatin + Aprepitant 3 mg/kg/day | 75 ± 5 | 35 ± 4 |
| Group 3. Cisplatin + Aprepitant 5 mg/kg/day | 60 ± 6 | 20 ± 4 |
| Group 4. Cisplatin + Aprepitant 6 mg/kg/day | 55 ± 6 | 10 ± 3 |
| Group 5. Cisplatin + Aprepitant 7 mg/kg/day | 40 ± 7 | 5 ± 2 |
| Group 6. Cisplatin + Aprepitant 8 mg/kg/day | 25 ± 4 | 0 ± 0 |
| Group 7. Cisplatin + Aprepitant 9 mg/kg/day | 10 ± 3 | 0 ± 0 |
| Group 8. Cisplatin + Aprepitant 10 mg/kg/day | 5 ± 1 | 0 ± 0 |

Example 12. Treatment with Non-Peptide NK1 Receptor Antagonists at Doses Between 1 and 10 mg Per Kilogram of Weight and Day, in Combination with Another Anti-Tumour Drug, Reduces the Size of Cancerous Tumours of Haemato-Lymphoid Cell Line (Leukaemias and Lymphomas) in Mammals To verify that the administration of the antagonists not of the NK1 receptors, at doses between 1 and 10 mg per kilogram of weight and day, in combination with other anti-tumour agents, reduces the sizes of haemato-lymphoid cell line tumours (leukaemias and lymphomas) in mammals, tumour cells were implanted in mice and were later treated with chemotherapeutic agents, alone and in combination with non-peptide NK1 receptor antagonists.

Immunocompromised female mice, 5-6 weeks of age were used, in the same conditions as explained in example 1. They were injected with $2 \times 10^7$ tumour cells, corresponding to a haemato-lymphoid cell line tumour (human lymphoma; reference BC-1; supplied by DSMZ) in 200 µl of PBS by subcutaneous route. The tumour size was measured and the mice were evaluated for their state of health and weight daily. The mice were randomized in nine groups when the tumours reached a volume of 75 mm³. One of the groups was treated with two single doses of Cisplatin, of 8 mg per kilogram of weight, on days 1 and 7 of the experiment (control group). The eight remaining groups were treated with the same treatment as the control group and the doses of 1 (group 1), 3 (group 2), 5 (group 3), 6 (group 4), 7 (group 5), 8 (group 6), 9 (group 7) and 10 (group 8) mg per kilogram of weight and day, of the NK1 receptor antagonist Aprepitant. 3 animals were treated per group, during 14 days. All the mice were sacrified at the end of the experiment. Table 12 shows the tumour size (in cubic millimeters±standard deviation) after 7 and 14 days of treatment, with each one of the doses used.

TABLE 12

Tumour size of the tumours provoked in an in vivo mouse model. Mean volume of the tumour in the control mice (untreated) or in the mice after treatment with the non-peptide NK1 receptor antagonist (Aprepitant).

| Human lymphoma cell line, reference BC-1. | 7 days | 14 days |
|---|---|---|
| Control. Cisplatin alone. | 85 ± 6 | 50 ± 3 |
| Group 1. Cisplatin + Aprepitant 1 mg/kg/day | 75 ± 3 | 40 ± 2 |
| Group 2. Cisplatin + Aprepitant 3 mg/kg/day | 60 ± 5 | 25 ± 2 |
| Group 3. Cisplatin + Aprepitant 5 mg/kg/day | 50 ± 5 | 10 ± 4 |
| Group 4. Cisplatin + Aprepitant 6 mg/kg/day | 45 ± 3 | 5 ± 2 |
| Group 5. Cisplatin + Aprepitant 7 mg/kg/day | 30 ± 2 | 0 ± 0 |
| Group 6. Cisplatin + Aprepitant 8 mg/kg/day | 20 ± 1 | 0 ± 0 |
| Group 7. Cisplatin + Aprepitant 9 mg/kg/day | 15 ± 1 | 0 ± 0 |
| Group 8. Cisplatin + Aprepitant 10 mg/kg/day | 10 ± 2 | 0 ± 0 |

Example 13. The NK1 Receptor Antagonists at Low Doses (Nanomolar Concentration Range) Increase the Proliferation of the Tumour Cells Cell cultures of various commercial tumour cell lines stated in table 13 were used.

TABLE 13

Human tumour cell lines used to demonstrate the action of the NK1 receptor antagonist at doses in nanomolar range.

| Type of tumour | Cell line | Selling company |
|---|---|---|
| Human adenocolon cancer | SW-403 | DSMZ |
| Human breast cancer | MT-3 | DSMZ |
| Human lung cancer | A-427 | DSMZ |
| Human fibrosarcoma | HT-1080 | DSMZ |
| Human glioma | GAMG | DSMZ |
| Human B cell lymphoma | BC-1 | DSMZ |
| Human melanoma | MEL HO | DSMZ |
| Human neuroblastoma | KELLY | DSMZ |

DSMZ: Deutsche Sammlung von Mikrorganismen and Zellkulturen.

The cell proliferation was evaluated by the compound tetrazolium 3-(4, 5-dimethylthiazol-2-yl)-5-(3-carboxymethoxyphenyl) 2-(4-sulfophenyl)-2H-tetrazolium (MTS) in accordance with the instructions provided by the manufacturer (Kit: "CellTiter 96 Aqueous One-Solution Cell Proliferation Assay" Promega, USA; complete protocol of use available at url: http://www.promega.com/resources/protocols/technical-bulletins/0/celltiter-96-aqueous-one-solution-cell-proliferation-assay-system-protocol/).

The number of cells was quantified using a Coulter counter. A blank sample (without cells) and a control sample (containing $10^4$ cell/ml) were included in the tumour cell culture plates. The culture plates were grown in the presence of increasing concentrations of non-peptide NK1 receptor antagonists. To obtain the staining in the proliferation assays, 20 µl of MTS were added to each one of the wells of the cell culture plates 90 minutes before reading the samples in a multiscan spectrophotometer (TECAN Spectra classic, Barcelona, Spain) at 492 nm (assay wavelength) and 690 nm (reference wavelength). The different doses were tested in duplicate and each experiment was performed in triplicate.

The antagonist Aprepitant was used at the following concentrations: 1 nanomolar -nM-, 5 nanomolar -nM- and 7 nanomolar -nM-.

Figure 1:
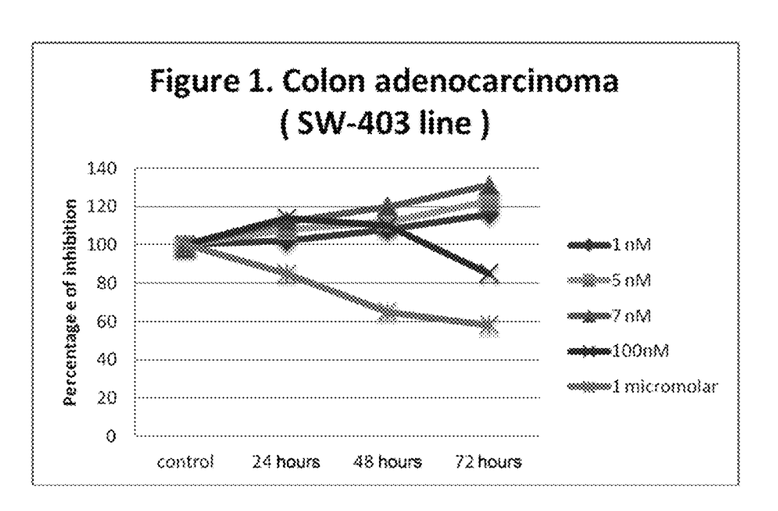
FIG. 1. NK1 receptor antagonists at low doses (nanomolar concentration range) increase the proliferation of human colon adenocarcinoma tumour cells.
Figure 2:
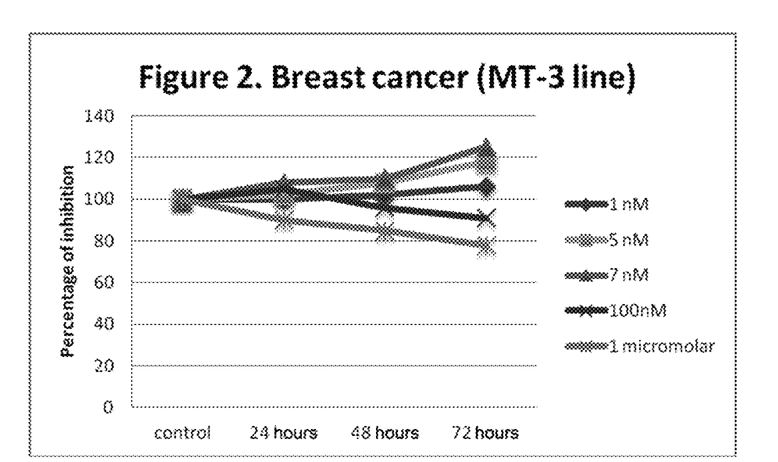
FIG. 2. NK1 receptor antagonists at low doses (nanomolar concentration range) increase the proliferation of human breast cancer tumour cells.
Figure 3:
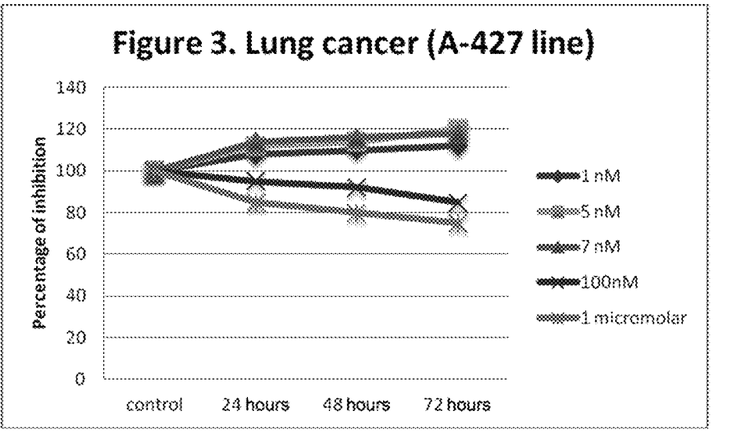
FIG. 3. NK1 receptor antagonists at low doses (nanomolar concentration range) increase the proliferation of human lung cancer tumour cells.
Figure 4:
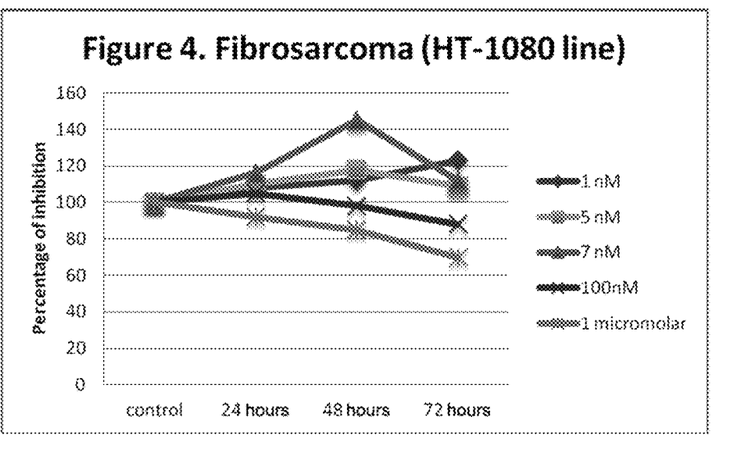
FIG. 4. NK1 receptor antagonists at low doses (nanomolar concentration range) increase the proliferation of tumour cells of the sarcomas (human fibrosarcoma).
Figure 5:
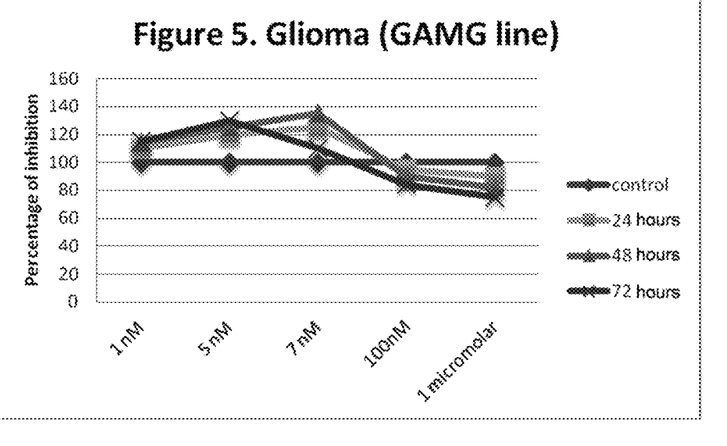
FIG. 5. NK1 receptor antagonists at low doses (nanomolar concentration range) increase the proliferation of human glioma tumour cells.
Figure 6:
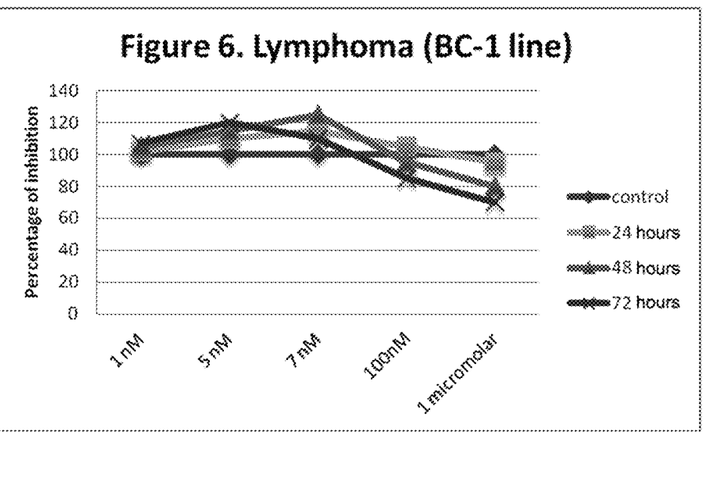
FIG. 6. NK1 receptor antagonists at low doses (nanomolar concentration range) increase the proliferation of lymphoma tumour cells (human B-cell lymphoma).
Figure 7:
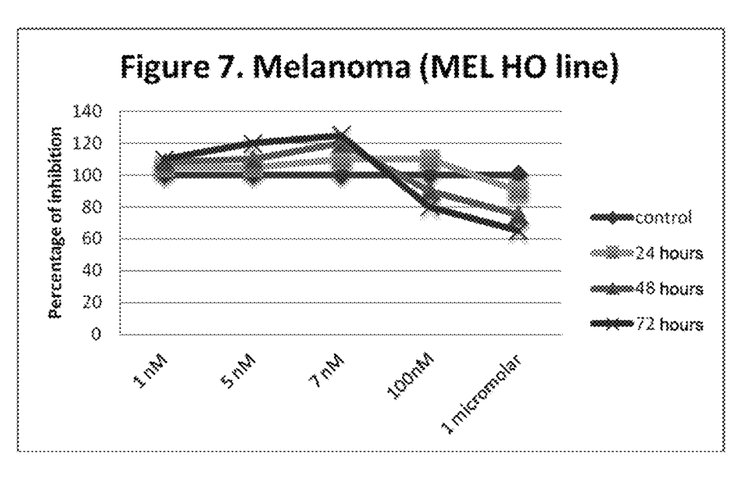
FIG. 7. NK1 receptor antagonists at low doses (nanomolar concentration range) increase the proliferation of human melanoma tumour cells.
Figure 8:
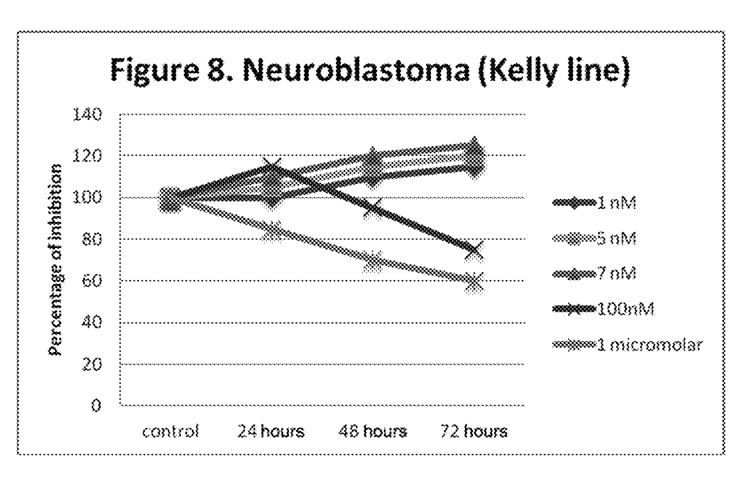
FIG. 8. NK1 receptor antagonists at low doses (nanomolar concentration range) increase the proliferation of the embryonal tumour cells (human neuroblastoma).

In all cases, an increase was observed of proliferation in the tumour cell line which was time dependant: greater inhibition in relation to longer antagonist exposure time. As proliferation control, the cells were grown in the absence of said antagonist. This is expressed in FIGS. 1 to 10.

The invention claimed is:

1. A method of treating cancerous tumors in a mammal, said method comprising administering a composition comprising aprepitant and cisplatin, wherein the dose of aprepitant administered is between 5 and 120 mg/kg of weight per day, wherein the cancerous tumors are selected from the list consisting of lung cancer, glioma, fibrosarcoma, lymphoma, melanoma, and neuroblastoma.

2. The method of claim 1, wherein the dose is between 8 and 100 mg/kg of weight per day.

3. The method of claim 2, wherein the dose is between 10 and 80 mg/kg of weight per day.

4. The method according to claim 1, wherein the composition further comprises a pharmaceutically acceptable carrier.

5. The method according to claim 1, wherein the cancerous tumors present with alteration of the peritumoral environment.

6. The method according to claim 5, wherein the cancerous tumors that present with peritumoral alteration show an increased synthesis of the markers selected from the group consisting of: NF-kB, EGF, VEGF, TNF-$\alpha$, TGF-$\alpha$, TGF-$\beta$ 1, TGF-$\beta$ 2, TGF-$\beta$ 3, SPARC, MMP-3; MMP-7, MMP-9, MMP-11, MMP-13, MMP-14, and combinations thereof.

7. The method according to claim 1, wherein the mammal is a human.

8. The method according to claim 1, wherein the dose of aprepitant administered is between 35 and 120 mg/kg of weight per day.

* * * * *